US00PP16384P2

(12) United States Plant Patent
Smith

(10) Patent No.: US PP16,384 P2
(45) Date of Patent: Mar. 28, 2006

(54) ***CHRYSANTHEMUM* PLANT NAMED 'GOLDEN YOANDREA'**

(50) Latin Name: *Chrysanthemum×morifolium*
Varietal Denomination: Golden Yoandrea

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 157 days.

(21) Appl. No.: 10/937,762

(22) Filed: Sep. 8, 2004

(51) Int. Cl.
*A01H 5/00* (2006.01)

(52) U.S. Cl. ..... Plt./289

(58) Field of Classification Search ..... Plt./289
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Chrysanthemum* plant named 'Golden Yoandrea', characterized by its upright, outwardly spreading and rounded plant habit; freely branching habit; freely flowering habit; decorative-type inflorescences with elongated oblong-shaped ray florets; golden yellow-colored ray florets; natural season flowering in mid-October in the Northern Hemisphere; and good garden performance.

2 Drawing Sheets

Botanical classification/cultivar designation: *Chrysanthemum×morifolium* cultivar Golden Yoandrea.

BACKGROUND OF THE INVENTION

The present invention relates to a new and distinct cultivar of *Chrysanthemum* plant, botanically known as *Chrysanthemum×morifolium*, commercially known as a garden-type *Chrysanthemum* and hereinafter referred to by the name 'Golden Yoandrea'.

The new *Chrysanthemum* is a naturally-occcurring whole plant mutation of the *Chrysanthemum×morifolium* cultivar Yoandrea, disclosed in U.S. Plant Pat. No. 12,983. The new *Chrysanthemum* was discovered and selected by the Inventor as a single flowering plant within a population of plants of the cultivar Yoandrea in a controlled environment in Alva, Fla. in November, 2000. The selection of this plant was based on its desirable inflorescence form, attractive floret coloration and good garden performance.

Asexual reproduction of the new cultivar by terminal vegetative cuttings in a controlled environment in Alva, Fla. since January, 2001, has shown that the unique features of this new *Chrysanthemum* are stable and reproduced true to type in successive generations.

SUMMARY OF THE INVENTION

The cultivar Golden Yoandrea has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Golden Yoandrea'. These characteristics in combination distinguish 'Golden Yoandrea' as a new and distinct cultivar of *Chrysanthemum:*

1. Upright, outwardly spreading and rounded plant habit.
2. Freely branching habit.

3. Freely flowering habit.
4. Decorative-type inflorescences with elongated oblong-shaped ray florets.
5. Golden yellow-colored ray florets.
6. Natural season flowering in mid-October in the Northern Hemisphere.
7. Good garden performance.

In side-by-side comparisons conducted in Alva, Fla. under natural season conditions, plants of the new *Chrysanthemum* differed from plants of the parent, the cultivar Yoandrea, in the following characteristics:

1. Plants of the new *Chrysanthemum* flowered about two days earlier than plants of the cultivar Yoandrea.
2. Plants of the new *Chrysanthemum* and the cultivar Yoandrea differed in ray floret coloration as ray florets of plants of the cultivar Yoandrea were orange in color.

Plants of the new *Chrysanthemum* can be compared to plants of the *Chrysanthemum* cultivar Golden Spotlight, disclosed in U.S. Plant Pat. No. 11,912. In side-by-side comparisons conducted in Alva, Fla. under natural season conditions, plants of the new *Chrysanthemum* differed from plants of the cultivar Golden Spotlight in the following characteristics:

1. Plants of the new *Chrysanthemum* were more outwardly spreading and denser than plants of the cultivar Golden Spotlight.
2. Plants of the new *Chrysanthemum* had smaller inflorescences than plants of the cultivar Golden Spotlight.
3. Plants of the new *Chrysanthemum* and the cultivar Golden Spotlight differed in ray floret coloration as plants of the cultivar Golden Spotlight tended to "pink" with development.
4. Plants of the new *Chrysanthemum* flowered about two weeks later than plants of the cultivar Golden Spotlight.

Plants of the new *Chrysanthemum* can also be compared to plants of the *Chrysanthemum* cultivar Cleagar gfl, disclosed in U.S. Plant Pat. No. 10,463. In side-by-side comparisons conducted in Alva, Fla. under natural season conditions, plants of the new *Chrysanthemum* differed from plants of the cultivar Cleagar gfl in the following characteristics:

1. Plants of the new *Chrysanthemum* were taller and more outwardly spreading than plants of the cultivar Cleagar gfl.
2. Plants of the new *Chrysanthemum* flowered about one week later than plants of the cultivar Cleagar gfl.
3. Plants of the new *Chrysanthemum* and the cultivar Cleagar gfl differed in ray floret coloration as plants of the cultivar Cleagar gfl had less intense yellow-colored ray florets.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of a typical flowering plant of 'Golden Yoandrea' grown in a container.

The photograph on the second sheet comprises a close-up view of typical inflorescences of the cultivar 'Golden Yoandrea'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Leamington, Ontario, Canada during the late summer and fall in an outdoor nursery and under conditions and practices which approximate those generally used in commercial garden-type *Chrysanthemum* production. One cutting was planted in a 15.25-cm container in mid-July. During the production of the plants, plants were exposed to natural season photoperiodic conditions with day temperatures averaging 26° C. and night averaging 18° C. Measurements and numerical values represent averages for typical flowering plants.

Botanical classification: *Chrysanthemum×morifolium* cultivar Golden Yoandrea.

Commercial classification: Decorative-type garden *Chrysanthemum*.

Parentage: Naturally-occurring whole plant mutation of the *Chrysanthemum×morifolium* cultivar Yoandrea, disclosed in U.S. Plant Pat. No. 12,983.

Propagation:

*Type.*—Terminal vegetative cuttings.

*Time to initiate roots, year-round.*—About four days at 21° C.

*Time to produce a rooted cutting, year-round.*—About ten to twelve days at 21° C.

*Root description.*—Fine, fibrous; white in color.

*Rooting habit.*—Freely branching.

Plant description:

*Plant form/growth habit.*—Perennial herbaceous decorative-type garden *Chrysanthemum*. Inverted triangle with rounded crown. Stems initially upright, then outwardly spreading. Freely branching with lateral branches potentially developing at every node. Moderately vigorous to vigorous.

*Plant height.*—About 18.5 cm.

*Plant diameter.*—About 28 cm.

*Lateral branches.*—Length: About 21 cm. Diameter: About 5 mm. Internode length: About 1.4 cm. Strength: Strong. Texture: Pubsecent. Color: Close to 144A.

*Foliage description.*—Leaf arrangement: Alternate. Length: About 3.4 cm. Width: About 2.75 cm. Apex: Mucronate. Base: Mostly truncate. Margin: Palmately and deeply lobed; sinuses mostly divergent. Texture, upper and lower surfaces: Pubescent. Color: Developing foliage, upper surface: More green than 147A. Developing foliage, lower surface: Close to 147B. Fully expanded foliage, upper surface: Close to 147A. Fully expanded foliage, lower surface: Close to 147B. Venation, upper surface: Close to 147A. Venation, lower surface: Close to 146A. Petiole: Length: About 7 mm. Diameter: About 3 mm. Texture, upper and lower surfaces: Pubescent. Color, upper surface: 147A to 146A. Color, lower surface: Close to 146A.

Inflorescence description:

*Appearance.*—Decorative-type inflorescence form with elongated oblong-shaped ray florets. Inflorescences borne on terminals above foliage, arising from leaf axils. Disc and ray florets developing acropetally on a capitulum. Inflorescences face mostly upright or outwardly. Inflorescences hemispherical in shape. Freely flowering habit; about 16 inflorescences and develop per lateral branch. Inflorescences persistent. Inflorescences not fragrant.

*Flowering response.*—Under natural season conditions, plants flower in mid-October in the Northern Hemisphere.

*Inflorescence bud (before showing color).*—Height: About 7 mm. Diameter: About 6 mm. Shape: Oblate. Color (lower surface of phyllaries): Close to 146A.

*Inflorescence size.*—Diameter: About 4.8 cm. Depth (height): About 2.25 cm. Disc diameter: Disc florets not observed. Receptacle diameter: About 5 mm. Receptacle height: About 5 mm.

*Ray florets.*—Shape: Elongated oblong. Length: About 2.4 cm. Corolla tube length: About 3.5 mm. Width: About 7 mm. Apex: Acute to emarginate. Margin: Fused. Texture: Smooth, glabrous; satiny. Surface: Concave. Orientation: Initially upright, then perpendicular to the peduncle. Number of ray florets per inflorescence: About 177 in numerous whorls. Color: When opening, upper and lower surfaces: Close to 12A overlain with close to 187A. Fully opened, upper surface: Close to 12A to 9A. Fully opened, lower surface: Close to 9B to 9C.

*Phyllaries.*—Quantity per inflorescence: About 24. Length: About 6 mm. Width: About 3 mm. Shape: Deltoid, elongated. Apex: Acute. Base: Truncate, fused. Margin: Entire. Texture, upper surface: Smooth, waxy. Texture, lower surface: Pubescent. Color, upper surface: Close to 144A. Color, lower surface: Close to 146A.

*Peduncle.*—Length: First peduncle: About 5.2 cm. Fourth penduncle: About 8.75 cm. Seventh peduncle: About 10.2 cm. Diameter: About 2 mm. Strength: Strong. Aspect: About 45° from vertical. Texture: Pubescent. Color: Close to 144A.

*Reproductive organs.*—Androecium: None observed. Gynoecium: Present on ray florets.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have been observed to be have good garden performance and to be tolerant to rain, wind and temperatures ranging from 0 to greater than 38° C.

It is claimed:

1. A new and distinct cultivar of *Chrysanthemum* plant named 'Golden Yoandrea', as illustrated and described.

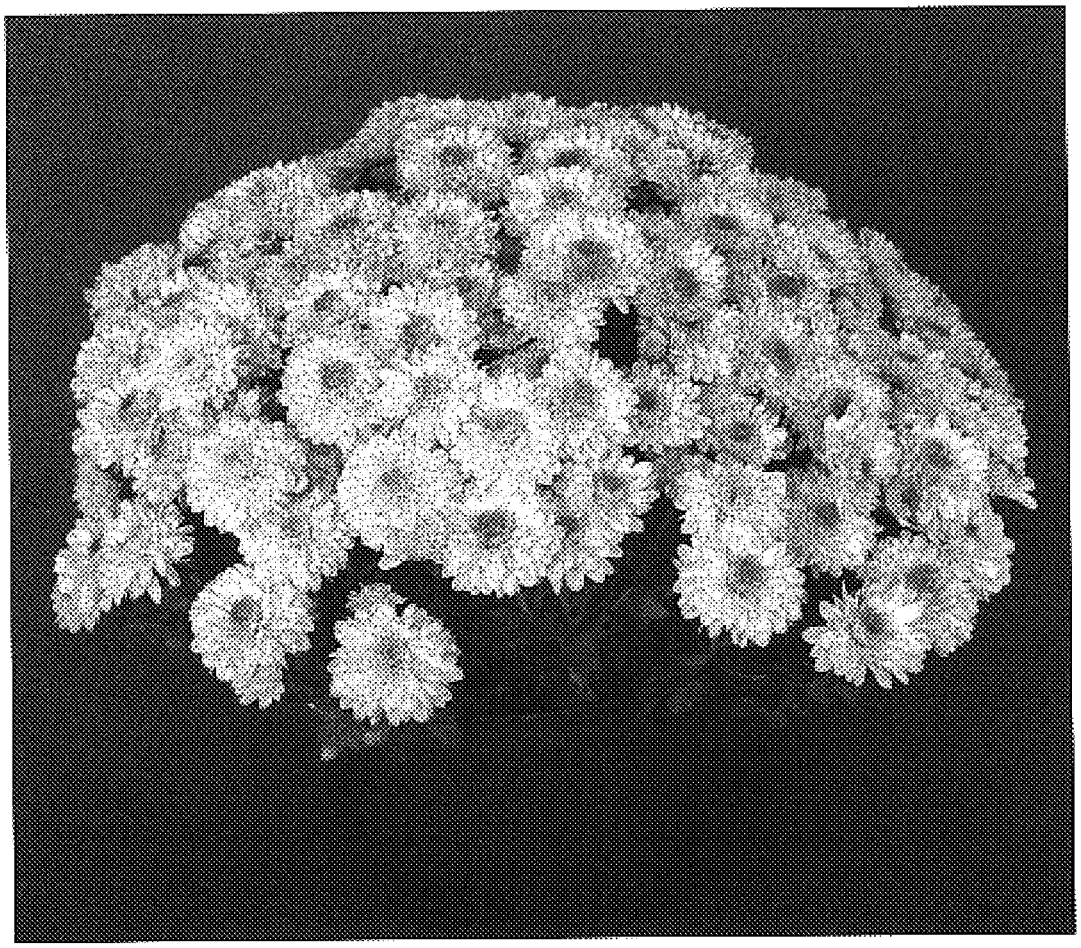

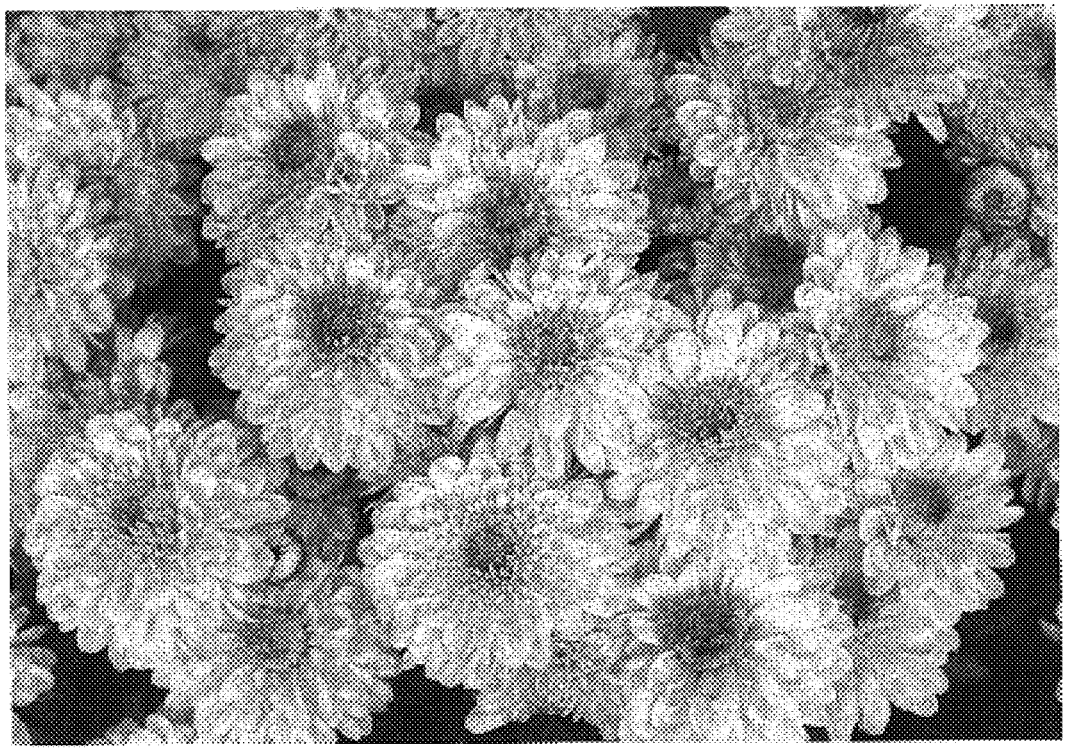

* * * * *